United States Patent
Carson (10) Patent No.: US 9,013,699 B2
(45) Date of Patent: Apr. 21, 2015

(54) VACCINE TESTING SYSTEM

(76) Inventor: Cantwell G. Carson, New York, NY (US)

(*) Notice: Subject to any disclaimer, the term of this patent is extended or adjusted under 35 U.S.C. 154(b) by 363 days.

(21) Appl. No.: 13/508,458

(22) PCT Filed: Nov. 8, 2010

(86) PCT No.: PCT/US2010/055846
§ 371 (c)(1),
(2), (4) Date: May 7, 2012

(87) PCT Pub. No.: WO2011/057198
PCT Pub. Date: May 12, 2011

(65) Prior Publication Data
US 2012/0224178 A1    Sep. 6, 2012

Related U.S. Application Data

(60) Provisional application No. 61/259,457, filed on Nov. 9, 2009.

(51) Int. Cl.
| | |
|---|---|
| G01N 21/00 | (2006.01) |
| C07K 16/28 | (2006.01) |
| A61K 39/00 | (2006.01) |
| G01N 21/59 | (2006.01) |

(52) U.S. Cl.
CPC ............ C07K 16/2803 (2013.01); A61K 39/00 (2013.01); G01N 21/59 (2013.01)

(58) Field of Classification Search
CPC .......................... G01N 31/229; G01N 21/51
USPC ................................................ 356/435, 343
See application file for complete search history.

(56) References Cited

U.S. PATENT DOCUMENTS

| | | | |
|---|---|---|---|
| 3,234,846 A | 2/1966 | Cropper et al. |
| 3,576,558 A | 4/1971 | Devries |
| 3,988,591 A | 10/1976 | Killer |
| 4,118,192 A | 10/1978 | Sawai et al. |
| 4,643,573 A | 2/1987 | McLachlan et al. |

(Continued)

OTHER PUBLICATIONS

Sirirat Techathawat, et al., Exposure to heat and freezing in the vaccine cold chain in Thailand, Science Direct, Vaccine 25 (2007) 1328-1333.

(Continued)

*Primary Examiner* — Kara E Geisel
(74) *Attorney, Agent, or Firm* — Smith Moore Leatherwood LLP; Thomas W. Epting (57) ABSTRACT

Several methods and apparatuses for determining whether a vaccine specimen has previously frozen. One method includes providing a known value correlating to the settling of vaccine known to have previously frozen, and, upon agitation of the specimen, directing light substantially through the specimen as the specimen settles. The amount of light that passes through the specimen correlates to the settling of the specimen and is compared to the known value to determine whether the specimen has previously frozen. Another method includes providing light of a predetermined wavelength and directing the light through the specimen. The intensity of the light transmitted through the specimen is compared to the intensity of light of the predetermined wavelength having passed through an amount of vaccine known to have previously frozen. Based on this comparison, a determination is made whether the specimen has previously frozen.

22 Claims, 7 Drawing Sheets

(56) References Cited

U.S. PATENT DOCUMENTS

| | | |
|---|---|---|
| 5,239,942 A | 8/1993 | Ignacio et al. |
| 5,328,822 A | 7/1994 | McKinney et al. |
| 5,453,832 A | 9/1995 | Joyce |
| 5,571,728 A | 11/1996 | Kraus |
| 6,404,500 B1 | 6/2002 | Schneider et al. |
| 6,472,214 B2 | 10/2002 | Patel |
| 6,567,166 B2 | 5/2003 | Ottens et al. |
| 6,803,594 B2 | 10/2004 | Spolaczyk et al. |
| 6,957,623 B2 | 10/2005 | Guisinger et al. |
| 7,343,872 B2 | 3/2008 | Taylor et al. |
| 7,400,407 B2 | 7/2008 | Ng et al. |
| 2001/0046048 A1* | 11/2001 | Harris et al. .......... 356/338 |
| 2006/0198761 A1 | 9/2006 | Tokhtuev et al. |
| 2006/0228369 A1* | 10/2006 | Chen .......... 424/184.1 |
| 2007/0076779 A1* | 4/2007 | Haarer .......... 374/101 |

OTHER PUBLICATIONS

Dipika M. Matthias, et al., Freezing temperatures in the vaccine cold chain: A systematic literature review, Science Direct, Vaccine 25 (2007) 3980-3986.

Martinus A.H. Capelle, et al., Spectroscopic characterization of antibodies absorbed to aluminium adjuvants: correlation with antibody vaccine immunogenicity, Science Direct, Vaccine 23 (2005) 1686-1694.

Unknown, supported by PATH's USAID-funded Health Tech program and its Children's Vaccine Program, Aug. 2003.

* cited by examiner

VACCINE TESTING SYSTEM

This application claims benefit of U.S. Provisional Application Ser. No. 61/259,547, filed Nov. 9, 2009, and the entirety of such application is incorporated herein by reference.

BACKGROUND

This invention relates generally to a vaccine testing system and method of determining the extent of temperature-induced damage in liquids, and in particular, liquid vaccines.

Freeze-sensitive vaccine preparations can potentially be damaged by freezing during storage and transport from their point of manufacture to their ultimate destination, this route sometimes being referred to as the pharmaceutical "cold chain."

Vaccines of various kinds employ the use of an adjuvant to enhance immunogenicity. This adjuvant, which could be, for example, micro-particulate aluminum hydroxide or aluminum phosphate, may be coated with a lattice of antigen. When thus attached, the antigen and adjuvant can reduce the dosage necessary to vaccinate, and thus extend vaccine supplies to ensure that more people can be vaccinated. However, if a vial of such a vaccine is frozen, the lattice of antigen may be removed from the adjuvant particles, and the antigen-adjuvant combination may be unable allow vaccinations at low dosages and, therefore, may be unusable.

The previously frozen adjuvant particles often agglomerate into larger clusters. This agglomeration is the basis for two current methods of determining whether an adjuvant-containing vaccine has been frozen previously. The first method is by phase-contrast microscopy, wherein the agglomerated adjuvant is clearly visible and distinguishable from non-agglomerated adjuvant. The second method is called the "shake test". The "shake test" relies on the faster sedimentation rate of the agglomerated adjuvant particles. The test vial and a known, reference frozen vial are shaken and placed side-by-side. The health worker then watches the two vials until he or she can say for certain whether or not the reference frozen vial is clarifying faster than the test vial. For example, ten and twenty dose vials can be tested in this manner in a matter of several minutes, but a one and two dose vial can take significantly longer before a reliable judgment can be made.

Although shown to be effective, these two methods can potentially have shortcomings. Because vaccines may be delivered to people in the poorest and most remote areas of the world, use of phase contrast microscopy may be impractical for wide use because of the cost and maintenance of a microscope.

The "shake test" is free and effective when carried out properly, but may also be prone to human error. If the health worker is impatient, he or she may not wait long enough to make a reliable judgment about whether a vaccine has been previously frozen or not, raising the likelihood of a false positive. The worker may also neglect to completely freeze the control vial, thereby potentially increasing the likelihood of a false negative. Neither the "shake test" nor phase-contrast microscopy is quantitative, capable of producing a number that can be used to compare a numerical value of one vial versus another.

One method attempting to resolve this problem has been to use freeze indicators. These indicators would provide a calibrated external indicator that a freezing event had taken place. Although these remain important components of the pharmaceutical cold chain, they may not be designed nor have the ability to determine the extent to which vaccine has actually been damaged by freezing temperatures.

SUMMARY

Generally, in one embodiment, the present invention relates to a method and apparatus for determining whether a freeze-sensitive vaccine presentation has been damaged by freezing during storage or transportation, and thus whether it should still be used or discarded.

One method of the present invention may be used in connection with vaccine formulations where agglomerates form from dispersed adjuvant particles in the event the vial has been frozen. These agglomerates have a faster settling rate, and thus tend to fall towards the bottom of the vial more quickly than the dispersed, non-agglomerated particles. As the agglomerated particles fall, the amount of light transmitted through the top of the dispersion increases with time. The rate of this increase can be compared against a known frozen, reference control vaccine to determine whether the vaccine specimen in question, or, suspect vaccine, is still safe to use.

The agglomerated particles also tend to scatter light at larger wavelengths than the non-agglomerated ones. Therefore, another method of the present invention can include a comparison of two different wavelengths of light, only one of which is scattered effectively by the agglomerates. By comparing the transmitted intensities of the two different wavelengths, an estimate can be made about whether agglomerates have formed. This method can also be adapted to use a single "agglomerate sensitive" wavelength and to thus compare the intensities at detectors configured to detect forward-scattered and side-scattered wavelengths.

In addition to potentially being faster, the methods of the present invention have the advantage of minimizing the human factors present when inspecting vials with the naked eye. The methods of the present invention can also incorporate means of error-checking to reduce the likelihood of false positive and false negative determinations.

Turbidity may be produced in a vaccine by the suspension of adjuvant particles. If the particles are well dispersed and initially suspended throughout a column of fluid, as they may be in a freshly shaken vial of unfrozen vaccine, there may likely be little change in the turbidity until a sedimentation boundary forms. However, if the vaccine has been frozen and some of the particles have begun to agglomerate, there may be a more significant change in turbidity.

A clarification rate can be calculated by comparing two turbidity measurements taken at different times. Thus, the clarification rates of two freshly shaken vaccine vials, one of which is known to have been frozen previously, can be compared. If these clarification rates are found to be sufficiently similar, the test vaccine is rejected. If the clarification rates are sufficiently different, than the test vaccine may be accepted. The health worker is then alerted to the status of the test vaccine. Routines can also be put in place to safeguard against false negatives by declaring "frozen vial" clarification rates that appear abnormally low as erroneous.

This method of the present invention allows for small variations in the intensity of the light source, sensitivity of the detector, or the time that the measurement is started. This is because such method compares the relative changes in turbidity, and not the absolute values themselves. Moreover, a system or single device can be produced in accordance with the present invention having accessories to properly receive any vaccine vial size.

The methods of the present invention should also permit multiple pairs of vaccine to be tested simultaneously.

BRIEF DESCRIPTION OF THE DRAWINGS

The drawings referenced herein form a part of the specification. Features shown in the drawings are meant as illustrative of some, but not all, embodiments of the invention, unless otherwise explicitly indicated, and implications to the contrary are otherwise not to be made. Although in the drawings like reference numerals correspond to similar, though not necessarily identical, components and/or features, for the sake of brevity, reference numerals or features having a previously described function may not necessarily be described in connection with other drawings in which such components and/or features appear.

DESCRIPTION OF PREFERRED EMBODIMENTS

In the following detailed description of exemplary embodiments of the invention, reference is made to the accompanying drawings that form a part hereof, and in which are shown by way of illustration specific exemplary embodiments in which the invention may be practiced. While these embodiments are described in sufficient detail to enable those skilled in the art to practice the invention, it will nevertheless be understood that no limitation of the scope of the present disclosure is thereby intended. Alterations and further modifications of the features illustrated herein, and additional applications of the principles illustrated herein, which would occur to one skilled in the relevant art and having possession of this disclosure, are to be considered within the scope of this disclosure. Specifically, other embodiments may be utilized, and logical, mechanical, electrical, electro-optical, software/firmware and other changes may be made without departing from the spirit or scope of the present invention. Accordingly, the following detailed description is not to be taken in a limiting sense.

Referring now to the drawings in detail, wherein like reference characters represent like elements or features throughout the various views, the vaccine testing system of the present invention is indicated generally in the figures by reference character 10.

As noted above, other embodiments of the present invention include a device that can use two different wavelengths, only one of which will be significantly scattered by the larger aggregates that form upon freezing. By comparing the intensities of these two wavelengths, whether or not a given vial has been damaged by freezing should become apparent. It is to be understood that the wavelengths used can be drawn from the entire electromagnetic spectrum, and can emanate from one wavelength or source or from multiple wavelengths or sources.

One embodiment of vaccine testing system 10 can also be configured to compare scattering of a beam of light from the light sources at two different angles relative to the beam passing through the specimen. Detectors could be placed, for example, at approximately 0 degrees and 90 degrees from the center of a vial relative to the illumination source. These could be called the "forward-scatter" and "side-scatter" detectors. An instantaneous comparison of the illumination striking the two detectors, respectively, would be taken. This ratio would deviate from its initial value if the suspect vaccine was damaged by freezing at some point.

If the acceptable ratios for different vaccines were known, then only one vaccine specimen would be needed for measurement. This reading would be immediate, removing the requirement that the health worker wait a specified period of time before a result is produced. Furthermore, this method does not require the exclusion of the two-vial settling rate comparison method discussed above.

Also, both of the methods of the present invention could be used in a single device, if desired or in conjunction with one another. One method could be solely used as a calibration method for calibrating the testing device, or both methods could be used generally simultaneously on a given vaccine specimen to gather more comprehensive data about such vaccine specimen.

Figure 1A:
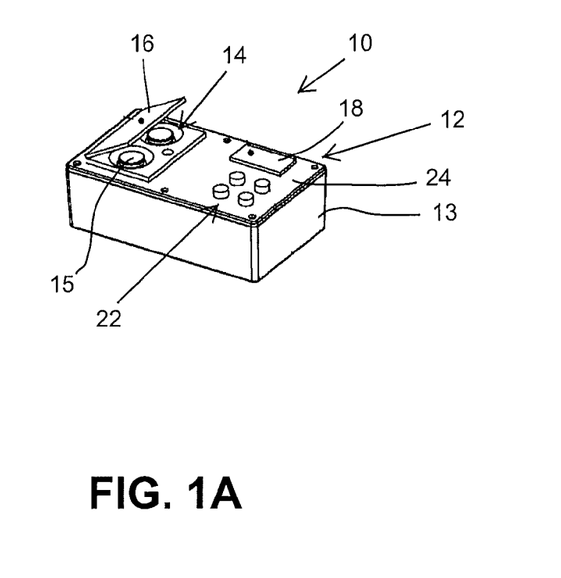
FIG. 1A is a perspective view of one embodiment of a vaccine testing system constructed in accordance with the present invention in a "closed" configuration.

Turning to FIG. 1A, one embodiment, a vaccine tester, generally 12, of the present invention, includes a cabinet, generally 13, a test compartment, for holding two vaccine vials, generally 14 and 15. A cover 16 is provided for covering test compartment 14 to block ambient light during vaccine testing. A solar cell 18 may be provided for charging a battery 20 (FIG. 1B) carried within cabinet 13 used to power vaccine tester 13. It is to be understood, however, that vaccine tester 12 could be powered solely by solar power, by alternating current power, by direct current power and/or a combination of the foregoing power sources.

Controls, generally 22, are provided on cover 24 for operating vaccine tester 12 in a manner described in more detail below.

Figure 1B:
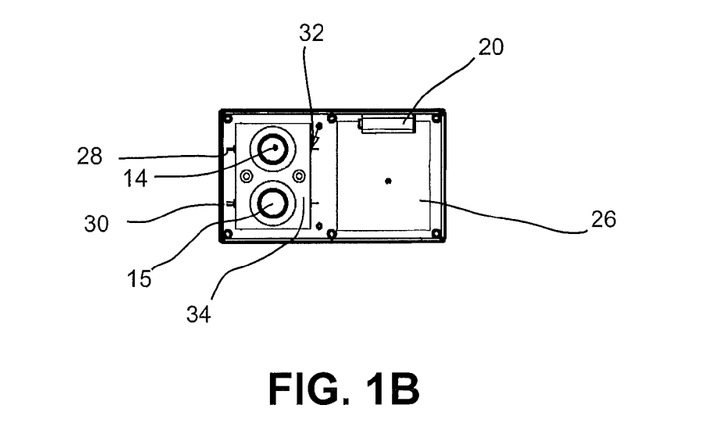
FIG. 1B is a plan view of a portion of the vaccine testing system shown in FIG. 1A in an "open" configuration.

FIG. 1B illustrates vaccine tester 12 with its cover 24 removed, exposing interior portions of vaccine tester 12 and circuit board 26. Vaccine vials 14 and 15 are shown in place for testing positioned between light sources, such as light emitting diodes (LEDs) 28, 30 and photoresistors or photocells 32, 34. It is to be understood that other light sources, such as lasers, could be used instead of or in addition to LEDs 28, 30, if desired.

Figure 2:
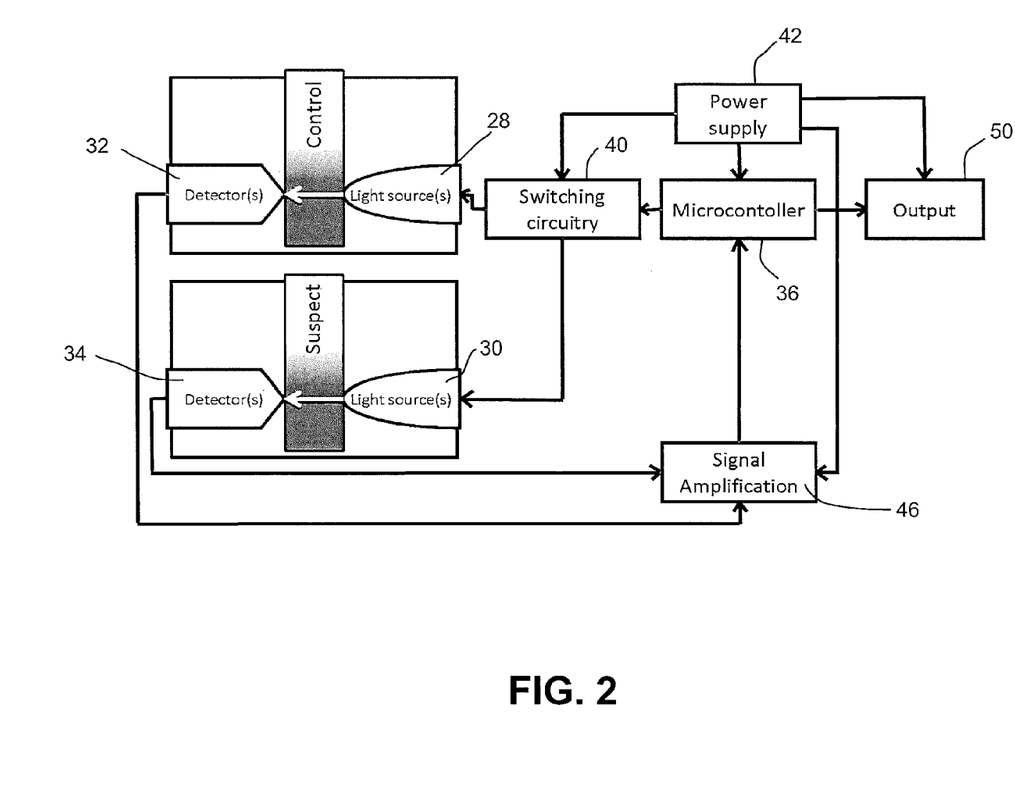
FIG. 2 is a schematic representation of one embodiment of a vaccine testing system constructed in accordance with the present invention.

FIG. 2 is a schematic representation of an embodiment of a vaccine testing system 10, such as vaccine tester 12, wherein the various components of vaccine tester 12 are depicted. Controls 22 interface with a processor, such as a computer, programmable logic controller, microcontroller, or the like, generally 36 to operate vaccine tester 12. Processor 36 may store known good/bad values for a variety of vaccines, their respective testing protocols, predetermined settling rates, testing calibration sequences, and other information. Vaccine tester 12 could be fully automated, wherein it performs a test sequence on the vaccine specimen once the vials are in place and cover 16 is closed and/or manually operated, where an operator performs a testing sequence using controls 22.

FIG. 2 illustrates LEDs 28, 30 being powered through switching circuitry, generally 40, from a power supply, 42. Power supply 42 powers processor 36, and processor 36 controls switching circuitry 40. Using the methodology disclosed herein, photo detectors, such as photo resisters 32, 34, receive light from LEDs 28, 30 as such light passes through a reference, or control, vaccine vial 14, and a vaccine specimen vial 15, and the output of photo resisters 32, 34 is amplified via an amplifier 46, the output of which goes to processor 36. Based on the output of photo resisters 32, 34, processor 36 generates an output based on the relative rates of clarification in vials 14 and 15 to an output device, generally 50, which could be a display and/or an audible emitter (not shown). By comparing the voltages from the two photodiodes or photoresistors 32, 34, the programmable microcontroller estimates whether the unknown vaccine vial has a lower sedimentation rate than the known frozen vaccine. The output from output device 50 is representative of whether the suspect vaccine specimen in vial 15 is good or not (in a go/no-go output configuration) and/or representative of a qualitative or quantitative value for such suspect vaccine.

Figure 3:
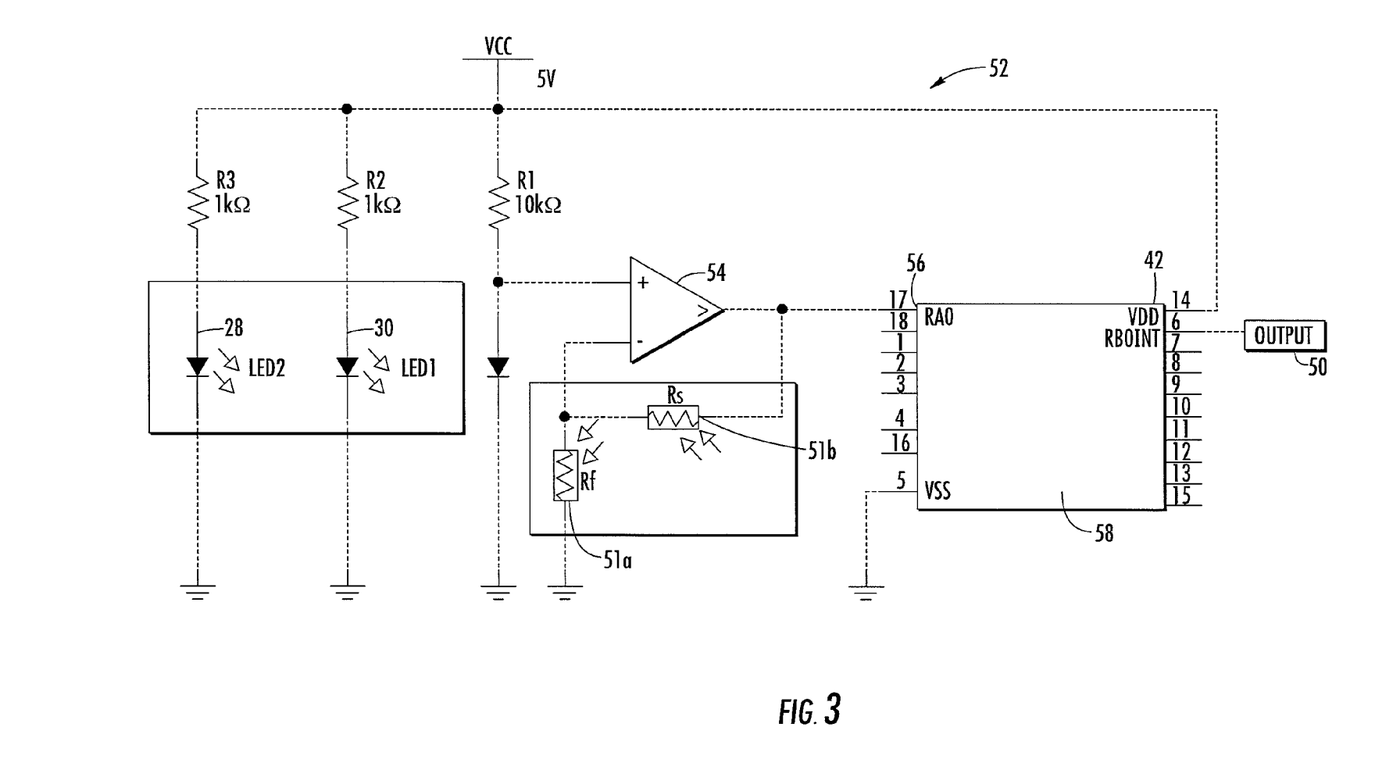
FIG. 3 is schematic representation of a circuit usable in one embodiment of a vaccine testing system constructed in accordance with the present invention.

FIG. 3 is a schematic representation of a circuit, generally 52, powered by voltage VCC (which could be, in one embodiment 5 volts) and usable inside one embodiment of a vaccine testing system 10, such as vaccine tester 12, and includes a photoresistors 51*a* for measuring the "known frozen" vaccine in vial 14, a photoresistor 51*b* for measuring the "suspect" vial 15, LED 28 for illuminating vial 12, LED 30 for illuminating vial 15, operational amplifier 54 for comparing voltages, a processor input 56 for operational amplifier 54 voltage, power supply 42, and an output device 50.

In FIG. 3, additional nomenclature provides that a photoresistor Rf measures the "known frozen" vial, and a photoresistor Rs measures the "suspect" vial. A light emitting diode LED1 illuminates the "known frozen" vial, and light emitting diode LED2 illuminates the "suspect" vial. Operational amplifier 54 compares voltages. Microcontroller input RA0 operational amplifier 54 voltage to a microcontroller 58. A power source VDD powers microcontroller 58, and microcontroller 58 provides an output signal via output RB0INT.

Figure 4:
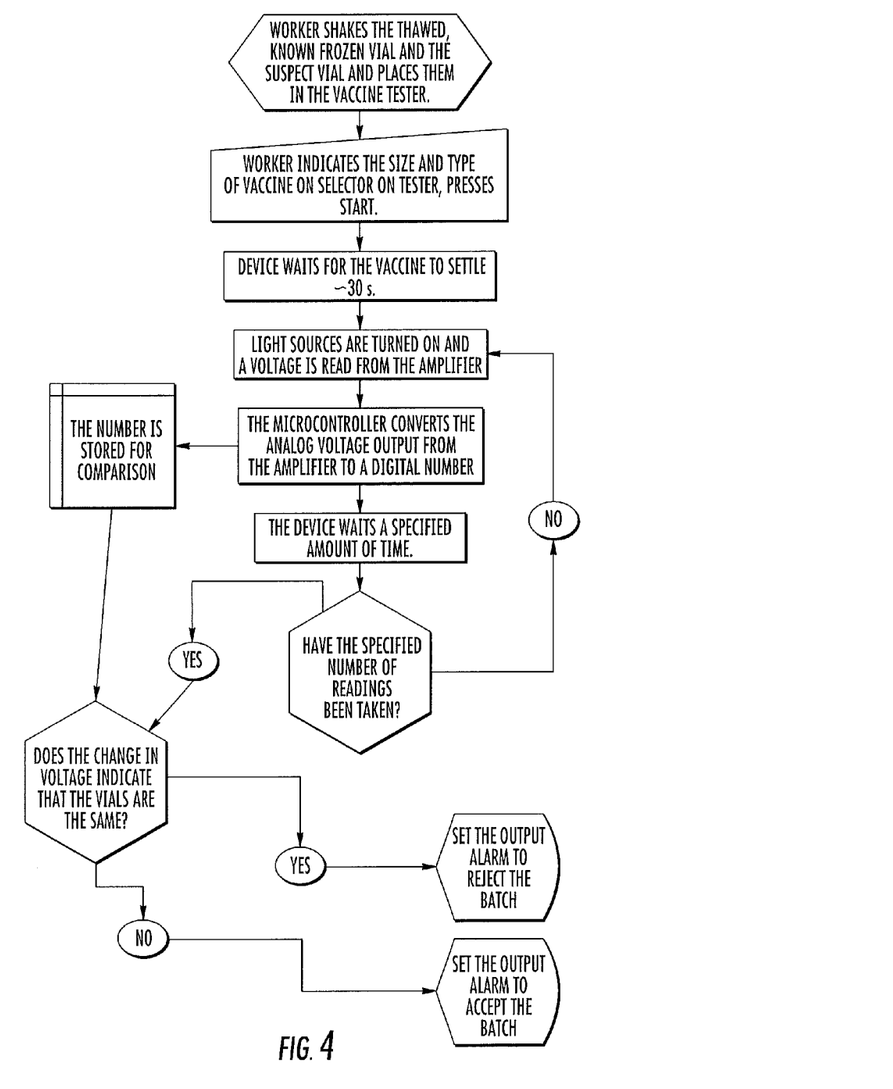
FIG. 4 is a schematic representation of a flow chart relating to one embodiment of a vaccine testing system constructed in accordance with the present invention.

FIG. 4 illustrates a flow chart, or decision tree, for operation of a vaccine testing system 10, such as vaccine tester 12, which could be used for comparing rates of clarification of vial 15 with respect to reference vial 14.

Figure 5:
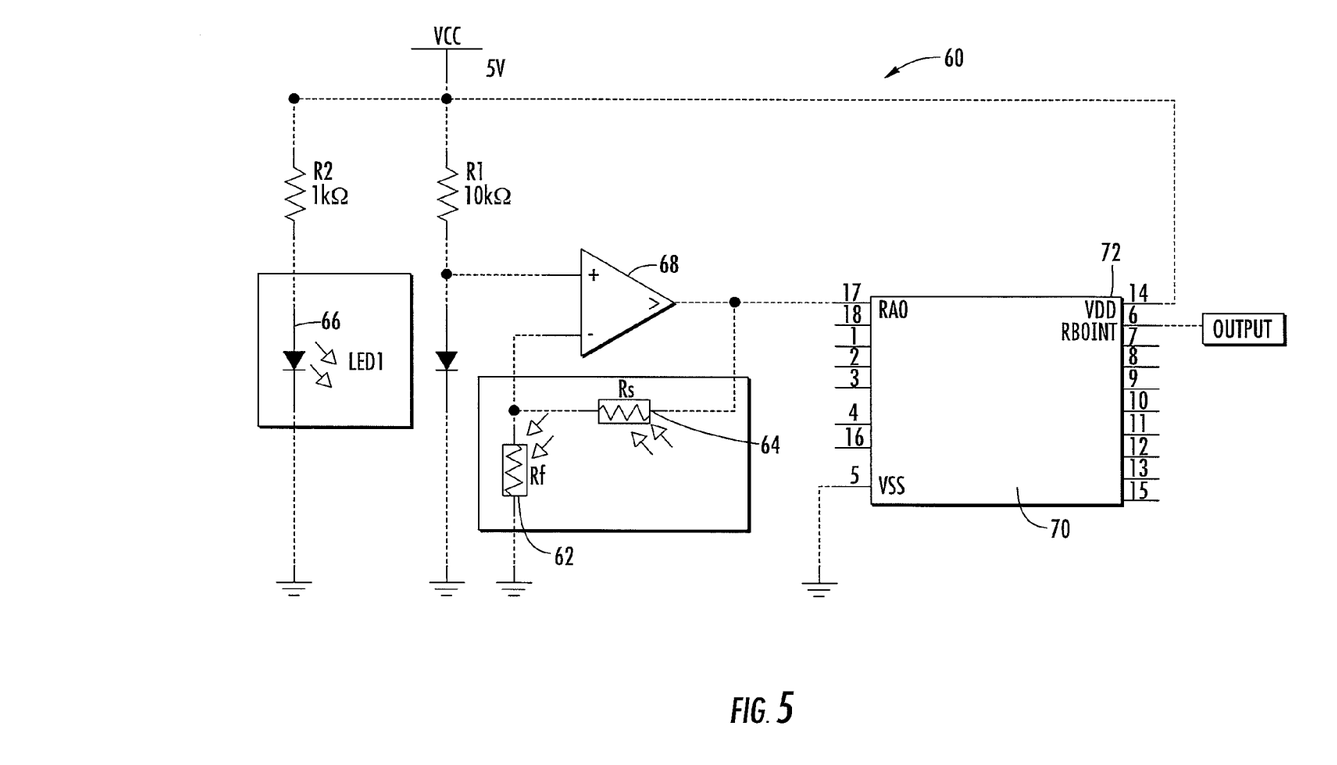
FIG. 5 is schematic representation of a circuit usable in an alternate embodiment of a vaccine testing system constructed in accordance with the present invention.

FIG. 5 is a schematic representation of a circuit, generally 60, powered by voltage VCC (which could be, in one embodiment 5 volts) and usable in an alternate embodiment of a vaccine testing system 10 for performing another method of the present invention, which includes a comparison of two different wavelengths of light, one of which being scattered effectively by the agglomerates. By comparing the transmitted intensities of the two different wavelengths, an estimate can be made about whether agglomerates have formed. This method can also be adapted to use a single "agglomerate sensitive" wavelength and to thus compare the intensities at detectors configured to detect forward-scattered and side-scattered wavelengths.

Circuit 60 includes a photoresistor 62 for measuring the "forward-scatter" light and a photoresistor 64 that measures the "side-scatter" light emanating from a light beam from LED 66, after such light passes through a suspect vaccine vial 15. Photoresistors 62, 64 can be positioned 0 degrees and 90 degrees, respectively, with respect to the light beam output from LED 66. An operational amplifier 68 compares voltages and outputs to a processor 70, which, in turn, outputs to an output device 70 representative of whether the suspect vaccine specimen in vial 15 is good or not (in a go/no-go output configuration) and/or representative of a qualitative or quantitative value for such suspect vaccine. A power source 72 powers circuit 62.

In FIG. 5, additional nomenclature provides that a photoresistor Rf measures the "forward-scatter" light, and photoresistor Rs measures the "side-scatter" light. Light emitting diode LED1 illuminates the "suspect" vial, and operational amplifier 70 compares voltages. Input RA0 to microcontroller 70 inputs operational amplifier 68 voltage. Power source VDD is for microcontroller 70, and output RB0INT outputs signals from microcontroller 70.

Figure 6:
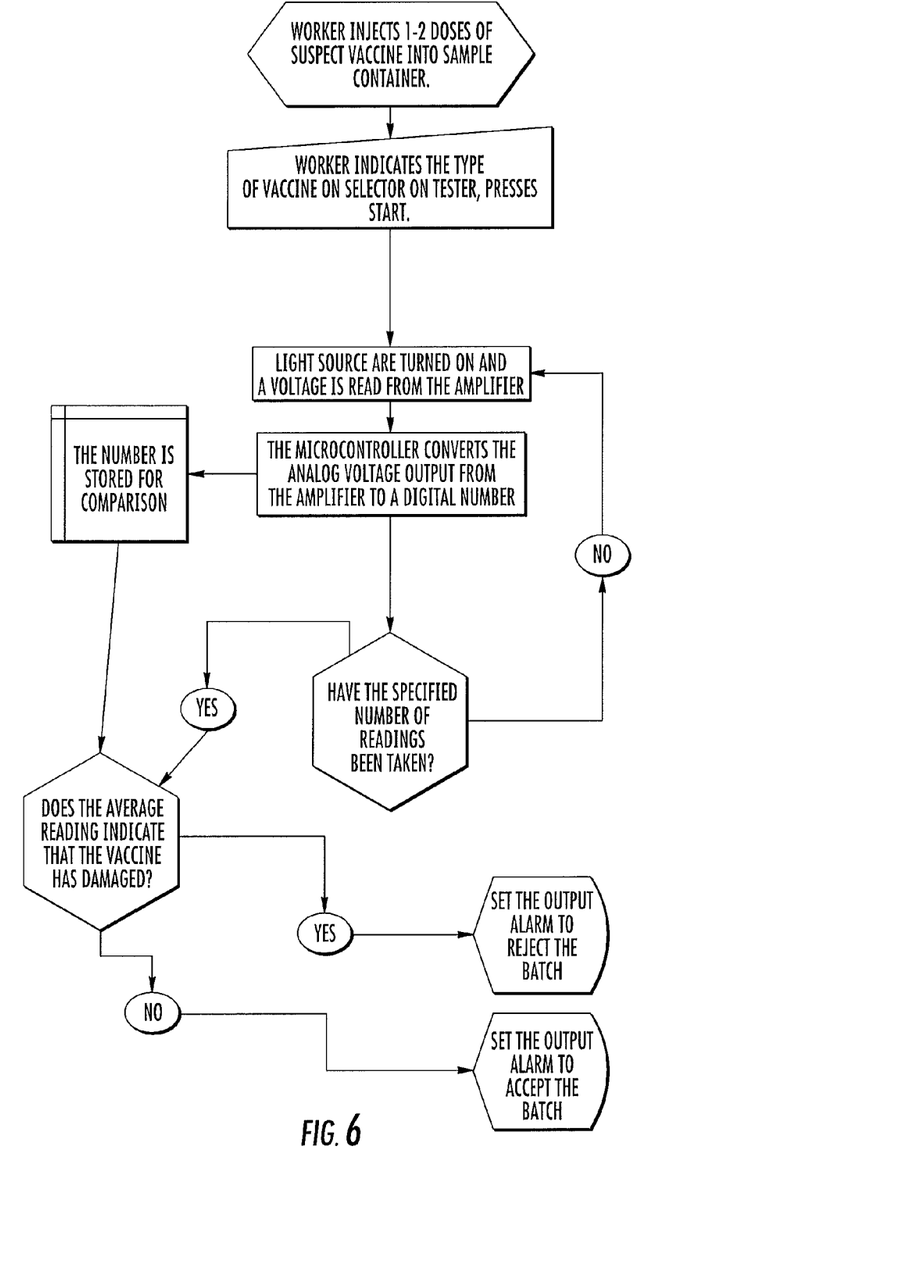
FIG. 6 is a schematic representation of a flow chart relating to the alternate embodiment of a vaccine testing system identified in FIG. 5.

FIG. 6 illustrates a flow chart, or decision tree, for operation of a vaccine testing system 10, such as provided by circuit 60, which could be used for comparison of at least one wavelength of light being scattered effectively by the agglomerates. By analyzing the side and forward scatter of light emanating from LED 64, an estimate can be made about whether agglomerates have formed and whether vaccine specimen in vial 15 is usable or not.

While vaccine tester 12 is a vaccine testing system 10 constructed in accordance with the present invention, it is to be understood that a vaccine testing system 10 constructed in accordance with the present invention could take on many different configurations and the present invention is not to be limited to the example configurations shown and disclosed herein.

By comparing the relative sedimentation rates of an unknown vaccine and known frozen vaccine specimens, a determination can be made about whether or not the unknown vaccine specimen has been damaged not only by freezing, but also, or alternately, by exposure to too much heat, since when a vaccine has been held at too high a temperature, the elevated temperature may cause the vaccine to denature, uncoiling the particles and causing the particles to remain in suspension for a longer period of time.

The photo-resistors discussed herein can be made arbitrarily sensitive by means of adjusting the resistance in a voltage divider circuit. As a result, such photo-resistors may be able to detect changes in opacity of vaccine specimens within a matter of seconds.

Because the conventional "shake test" may require as much as 10 to 15 minutes to complete, the vaccine testing system 10 is believed to constitute a qualitative improvement in the way that vaccines have been tested for freeze and/or other extreme temperature damage.

Vaccine testing system 10 can also be configured to output a sedimentation profile over time. This means that vaccine testing system 10 also potentially provides a quantitative method to examine and study the extent of freeze and/or other extreme temperature damage in a given vaccine specimen.

Because of its relatively straightforward construction, vaccine testing system 10 can also be constructed at a sufficiently low cost as to make it a viable alternative for situations where the manual "shake test" has been shown to be problematic.

It is to be understood that the vaccine testing system 10 can be used in connection with the testing of other liquids having particles therein for testing or otherwise determining sedimentation rates of such particles.

It is also to be understood that a vaccine testing system 10 can be programmed to tolerate a certain amount of apparent freeze damage in cases where only partial freezing has occurred.

EXAMPLE

Figure 7:
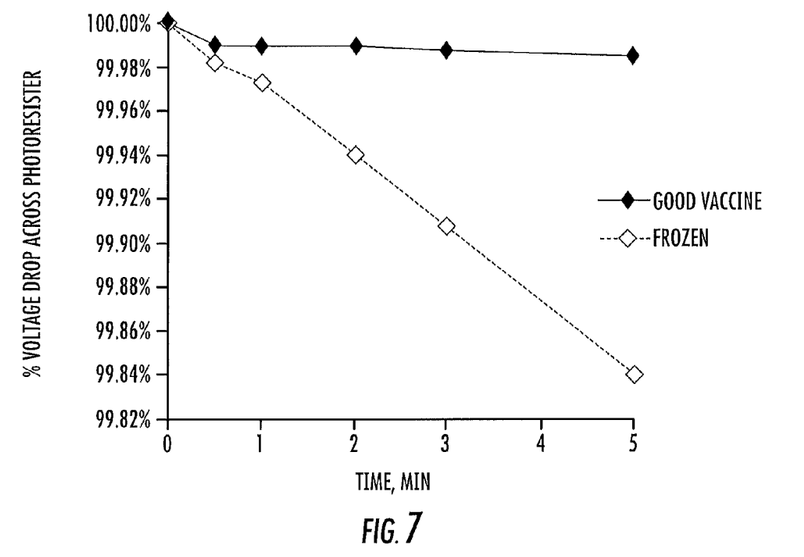
FIG. 7 is a graphical representation of data collected using an embodiment of the present invention.

In one potential example (which should not be construed to limit in any way the scope of the present invention) using an embodiment of the present invention, data was collected regarding sample vaccine vials using a device constructed in accordance with the present invention. FIG. 7 shows the manually collected data from the device. The vaccine that has been damaged displays a much higher rate of clarification than the vaccine that has not. Though the percent changes are small, these can be improved by increasing the gain across the photoresistor and possibly by using a brighter light source.

While preferred embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the teachings hereof.

What is claimed is:

1. A method of determining whether at least one specimen of a liquid vaccine has been previously frozen, the method comprising:
    providing a predetermined value correlating to the settling rate of an amount of said vaccine known to have previously frozen;
    providing at least one light source that emits light;
    providing at least one light detector that receives said light from said light source;
    agitating said specimen of said vaccine and then allowing said specimen to settle;
    directing said light substantially through said specimen as said specimen settles;
    outputting a test value from said light detector correlated to said light received by said light detector that passed through said specimen;
    performing a comparison between said test value and said predetermined value; and
    based on said comparison, determining whether said specimen has been previously frozen.

2. The method as defined in claim 1, further comprising outputting multiple values from said light detector that correlate to a sedimentation profile of said specimen.

3. A method of determining whether at least one specimen of a liquid vaccine has been previously frozen, the method comprising:
    providing a light source that emits light of a predetermined wavelength;
    providing at least one light detector;
    directing said light substantially through said at least one specimen;
    detecting with said at least one light detector said light that passes through said at least one specimen;
    outputting at least one test value from said at least one detector that correlates to the intensity of said light that passed through said at least one specimen;
    providing at least one reference value correlating to the intensity of light of said predetermined wavelength which passed through an amount of said vaccine known to have been previously frozen;
    performing a comparison of said at least one test value and said at least one reference value; and
    based on said comparison, determining whether said at least one specimen has previously frozen.

4. The method as defined in claim 3, wherein said providing of at least one light detector includes providing a first light detector and a second light detector separated from said first light detector.

5. The method as defined in claim 3, wherein:
    said providing of at least one light detector includes providing a first light detector and a second light detector separated from said first detector;
    detecting with said first light detector the forward scatter of said light that passes through said specimen; and
    detecting with said second light detector the side scatter of said light that passes through said specimen.

6. The method as defined in claim 3, wherein said specimen defines a central axis and wherein said providing of at least one light detector includes providing a first light detector and a second light detector separated from said first light detector by approximately 90 degrees with respect to said central axis.

7. The method as defined in claim 3, wherein said at least one specimen includes multiple specimens.

8. A method of determining whether at least one specimen of a liquid vaccine has been previously frozen, the method comprising:
    providing a first light source that emits light of a first predetermined wavelength;
    providing a second light source that emits light of a second predetermined wavelength differing from said first predetermined wavelength;
    directing said light of said first predetermined wavelength and said light of said second predetermined wavelength substantially through said specimen;
    providing at least one light detector that receives said first light and said second light that passed through said specimen;
    outputting a first test value from said light detector that correlates to the intensity of said first light that has passed through said specimen;
    outputting a second test value from said light detector that correlates to the intensity of said second light that has passed through said specimen;
    performing a comparison of said first test value and said second test value; and
    based on said comparison, determining whether said specimen has been previously frozen.

9. An apparatus for determining whether at least one specimen of a vaccine has been previously frozen, the apparatus comprising:
    a housing having a receptacle that receives said at least one specimen;
    a light source that emits light which substantially passes though said at least one specimen;
    at least one detector that receives said light from said light source and outputs a test value correlated to the settling of said specimen;
    at least one processor that compares said test value to a predetermined value correlating to the settling of an amount of said vaccine known to have previously frozen; and
    an indicator connected to said processor that indicates whether said at least one specimen has been previously frozen.

10. The apparatus as defined in claim 9, further comprising a power solar cell power source.

11. The apparatus as defined in claim 9, wherein said light source is at least one light emitting diode.

12. The apparatus as defined in claim 9, wherein said at least one detector is a photoresistor.

13. The apparatus as defined in claim 9, wherein said processor is a microcontroller.

14. The apparatus as defined in claim 9, wherein said indicator is an audio emitter.

15. The apparatus as defined in claim 9, wherein said indicator is a visual display.

16. The apparatus as defined in claim 9, wherein said light source is at least one laser.

17. The apparatus as defined in claim 9, wherein said processor includes stored predetermined settling values for a variety of vaccines.

18. The apparatus as defined in claim 9, further comprising:
a cover that moves between and open position and a closed position to cover said receptacle and said specimen; and
said cover being configured to energize said light source, said detector, and said processor upon being in said closed position.

19. A method of determining whether at least one specimen of a liquid vaccine has been previously frozen, the method comprising:
providing a predetermined value correlating to the settling rate of an amount of said vaccine known to have previously frozen;
providing a light source that emits light;
providing a detector that receives said light from said light source;
agitating said specimen of said vaccine and then allowing said specimen to settle;
directing said light substantially through said specimen as said specimen settles;
outputting a test value from said detector correlated to said light received by said detector that has passed through said specimen;
performing a comparison between said test value and said predetermined value; and
based on said comparison, determining whether said specimen has been previously frozen.

20. A method of determining whether at least one specimen of a medical liquid that has been previously frozen, the method comprising:
providing a light source that emits light of a predetermined wavelength;
providing at least one light detector;
directing said light substantially through said at least one specimen;
detecting with said at least one light detector said light that passes through said specimen;
outputting at least one test value from said at least one detector that correlates to the intensity of said light that passed through said at least one specimen;
providing at least one reference value correlating to the intensity of light of said predetermined wavelength which passed through an amount of said medical liquid known to have previously frozen;
performing a comparison between said at least one test value and said at least one reference value; and
based on said comparison, determining whether said at least one specimen has been previously frozen.

21. A method of determining whether at least one specimen of a liquid vaccine has been previously frozen, the method comprising:
providing a predetermined value correlating to the settling rate of an amount of said vaccine known to have previously frozen;
providing a first light source that emits a first light;
agitating said specimen of said vaccine and then allowing said specimen to settle;
providing a first detector that receives said first light from said first light source;
directing said first light substantially through said specimen as said specimen settles;
outputting a first test value from said first detector correlated to said first light received by said first detector that passed through said specimen;
performing a comparison between said first test value and said predetermined value;
based on said comparison of said first test value and said predetermined value, making a determination of whether said specimen has been previously frozen;
providing a second light source that emits a second light of a predetermined wavelength;
providing a second light detector;
directing said second light substantially through said specimen;
detecting with said second light detector said second light that passes through said specimen;
outputting a second test value from s second detector that correlates to the intensity of said second light that passed through said specimen;
providing a reference value correlating to the intensity of light of said predetermined wavelength which passed through an amount of said vaccine known to have previously frozen;
performing a comparison between said second test value to said reference value; and
based on said comparison between said second test value and said reference value, determining whether said specimen has been previously frozen.

22. An apparatus for determining whether at least one specimen of a liquid vaccine has been previously frozen, the apparatus comprising:
a housing having a receptacle that receives said at least one specimen;
a light source that emits light of a predetermined wavelength substantially through said specimen;
at least one light detector that receives said light and that outputs a test value correlated to the intensity of said light that passed through said specimen;
at least one processor that compares said test value to the intensity of light of said predetermined wavelength having passed through an amount of said vaccine known to have previously frozen; and
an indicator connected to said processor that indicates whether said specimen has been previously frozen.

* * * * *